United States Patent [19]

Schromm et al.

[11] 4,241,068

[45] Dec. 23, 1980

[54] 2-(PYRIDYL-AMINO)-BENZOIC ACIDS AND SALTS THEREOF

[75] Inventors: Kurt Schromm, Ingelheim; Anton Mentrup, Mainz-Kastel; Ernst-Otto Renth; Armin Fügner, both of Ingelheim; Volker Jacobi, Gau-Algesheim, all of Fed. Rep. of Germany

[73] Assignee: Boehringer Ingelheim GmbH, Ingelheim am Rhein, Fed. Rep. of Germany

[21] Appl. No.: 64,355

[22] Filed: Aug. 7, 1979

Related U.S. Application Data

[63] Continuation of Ser. No. 929,664, Jul. 31, 1978, abandoned.

[30] Foreign Application Priority Data

Aug. 10, 1977 [DE] Fed. Rep. of Germany ....... 2735919

[51] Int. Cl.³ .................. A61K 31/44; A61K 31/455; C07D 213/74; C07D 213/80
[52] U.S. Cl. ..................................... 424/263; 424/251; 424/258; 424/266; 544/284; 544/287; 544/292; 544/321; 544/331; 544/332; 546/141; 546/143; 546/153; 546/161; 546/276; 546/289; 546/291; 546/292; 546/297; 546/309; 546/310; 546/312
[58] Field of Search .............. 546/276, 289, 291, 292, 546/297, 309, 310, 312; 424/263, 266

[56] References Cited

U.S. PATENT DOCUMENTS 3,415,834  12/1968  Hoffmann et al. ................... 546/310

FOREIGN PATENT DOCUMENTS 2409260  1/1975  Fed. Rep. of Germany ........... 546/310
1162287  8/1969  United Kingdom ..................... 546/310
1264798  2/1972  United Kingdom ..................... 546/276

*Primary Examiner*—Richard Raymond
*Attorney, Agent, or Firm*—Hammond & Littell, Weissenberger & Muserlian

[57] ABSTRACT

Compounds of the formula

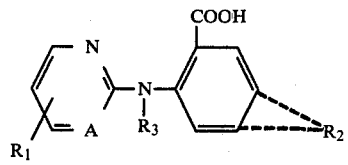

wherein
A is =CH— or =N—;
$R_1$ is (a) hydrogen, lower alkyl, lower alkoxy or a fused benzene ring, or (b) —CO—$R_4$, tetrazol-5-yl or cyano in the 4- or 5-position;
$R_2$ is —CO—$R_4$, tetrazol-5-yl, cyano or, when $R_1$ has one of the meanings included in (b), also hydrogen, lower alkyl, lower alkoxy or a fused benzene ring;
$R_3$ is hydrogen or lower alkanoyl; and
$R_4$ is hydroxyl, amino, hydroxy-amino, tetrazol-5-yl-amino or lower alkoxy;

internal salts thereof, and non-toxic salts thereof formed with a basic substance. The compounds as well as their salts are useful as antiallergics.

6 Claims, No Drawings

2-(PYRIDYL-AMINO)-BENZOIC ACIDS AND SALTS THEREOF

This is a continuation of copending application Ser. No. 929,664, filed July 31, 1978, now abandoned.

This invention relates to novel 2-(pyridyl- or pyrimidyl-amino)-benzoic acids and salts thereof, as well as to methods of preparing these compounds, pharmaceutical compositions containing them as active ingredients, and methods of using them as antiallergics.

More particularly, the present invention relates to a novel class of compounds represented by the formula

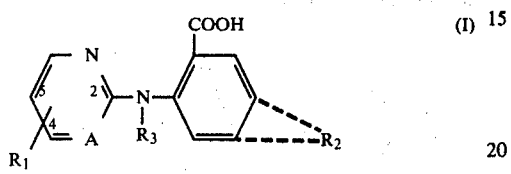

wherein
A is =CH— or =N—;
$R_1$ is (a) hydrogen, lower alkyl, lower alkoxy or a fused benzene ring, or (b) —CO–$R_4$, tetrazol-5-yl or cyano in the 4- or 5 - position;
$R_2$ is —CO–$R_4$, tetrazol -5-yl, cyano or, when $R_1$ has one of the meanings included in (b), also hydrogen, lower alkyl, lower alkoxy or a fused benzene ring;
$R_3$ is hydrogen or lower alkanoyl; and
$R_4$ is hydroxyl, amino, hydroxy-amino, tetrazol-5-yl-amino or lower alkoxy;
internal salts thereof, or salts thereof formed with a basic substance.

The terms "lower alkyl", "lower alkoxy" and "lower alkanoyl" as used herein are intended to designate those with 1 to 4 carbon atoms, where the hydrocarbon chain may be straight or branched. Specific examples thereof are methyl, ethyl, propyl, isopropyl, n-butyl, isobutyl, tert, butyl, methoxy, ethoxy, propoxy, isopropoxy, n-butoxy, isobutoxy, tert. butoxy, formyl, acetyl, propionyl and butyryl.

Preferred embodiments of $R_1$ and $R_2$ are hydrogen, a fused benzene ring, tertrazol-5-yl and carboxyl. The preferred embodiment of $R_3$ is hydrogen.

The compounds embraced by formula I may be prepared by the following methods:

Method A

By oxidizing a compound of the formula

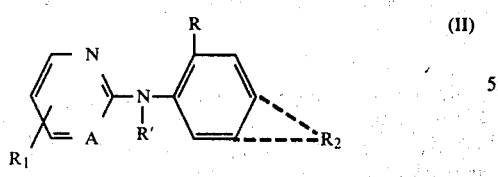

wherein
A, $R_1$ and $R_2$ have the same meanings as in formula I,
R is a substituent which can be converted into —COOH by oxidation, and
R' is lower alkanoyl,
and optionally splitting off the N- alkanoyl radical.

The oxidation is carried out with a strong oxidizing agent, such as with an aqueous solution of potassium permanganate buffered with magnesium sulfate. The reaction temperature is preferably between room temperature and the boiling point of the reaction mixture.

The substituent R may be an aliphatic hydrocarbon radical, especially lower alkyl such as methyl, or an unsaturated hydrocarbon radical, or also a partially oxidized hydrocarbon radical such as a hydroxy-, oxo- or halo-substituted hydrocarbon radical.

The removal of the alkanoyl substituent from the bridge nitrogen atom is effected by alkaline hydrolysis, for example with potassium hydroxide.

The starting compounds of the formula II may be prepared by known methods, for instance by reacting a 2-halo-pyridine or -pyrimidine with a derivative of o-toluidine, followed by acylation.

Method B

By subjecting a compound of the formula

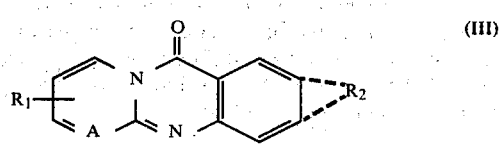

wherein A, $R_1$ and $R_2$ have the same meanings as in formula I, to ring cleavage with a base, especially with an alkali metal hydroxide, such as sodium hydroxide or potassium hydroxide. The reaction temperature is preferably between room temperature and the boiling point of the reaction mixture.

The starting compounds of the formula III may be obtained by known methods, such as by the process described in German Offenlegungsschrift No. 2,557,425.

Method C

By converting a compound of the formula

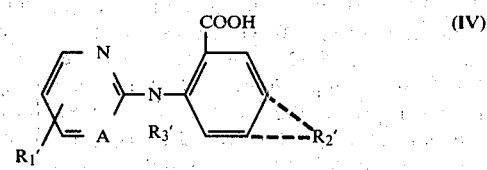

wherein
$R_1'$ has the meanings defined for $R_1$ in formula I or is a precursor of any of these;
$R_2'$ has the meanings defined for $R_2$ in formula I or is a precursor of one of these; and
$R_3'$ has the meanings defined for $R_3$ in formula I or is a precursor of one of these;
provided that at least one of $R_1'$, $R_2'$ and $R_3'$ is a precursor, into a compound of the formula I.

Examples of precursors of the amides, hydroxamic acids or esters are the corresponding esters which can be converted with ammonia, hydroxylamine or amino-tetrazole, respectively, or by transesterification. Nitriles can be converted into the corresponding tetrazol-5-yl compounds by reaction with sodium azide. Carbamoyl compounds can serve as precursors of the corresponding cyano compounds. Compounds of the formula IV in which $R_1'$ and/or $R_2'$ have the meanings defined for R in formula II can be converted into the corresponding compounds of the formula I wherein $R_1$ and/or $R_2$ are carboxyl by oxidation under the conditions described in method A. The alkaline hydrolysis described in method A can also be used for conversion of compounds with ester or carbamoyl groups into the corresponding carboxyl-substituted compounds.

If R₃ in the end product of the formula I is to be hydrogen, then R₃' in formula IV can be a substituent which may be split off by alkaline hydrolysis or hydrogenation, such as acyl or benzyl. On the other hand, if R₃ in the end product is to be alkanoyl then R₃' can be hydrogen.

The starting compounds of the formula IV are accessible by known processes.

Preferred embodiments of non-toxic salts of the compounds of the formula I are those formed with an alkali metal base or alkaline earth metal base, such as potassium hydroxide, or sodium hydroxide, or with a strong organic base, such as a lower alkylamine, ethanolamine or di- or triethanolamine.

The following examples illustrate the present invention and will enable others skilled in the art to understand it more completely. It should be understood, however, that the invention is not limited solely to the particular examples given below.

EXAMPLE 1

Dipotassium salt of 4-(2-pyridyl-amino)-isophthalic acid by method A (a) 4.8 gm of N-(2-pyridyl)-2,4-dimethylacetanilide, m.p. 46°–50° C. (prepared by reacting 2-chloropyridine with 2,4-dimethyl-aniline at 160°–170° C. and subsequent acetylation with acetic acid anhydride), and 2.4 gm of magnesium sulfate were dissolved in water, and the solution was heated to 30° C. 12.64 gm of potassium permanganate were added in portions to the warm solution, and the mixture was stirred for two hours on a water bath at 80°–90° C. Thereafter, while the mixture was still hot, the precipitated manganese dioxide was separated by suction filtration and washed with water. The filtrate was evaporated to a volume of 50 ml and then diluted with 50 ml of ethanol, and the potassium sulfate precipitated thereby was separated by suction filtration. The aqueous ethanolic filtrate was evaporated in vacuo, and the residue was crystallized with ethanol/ether, yielding the dipotassium salt of 4-[N-acetyl-N(2-pyridyl)-amino]-isophthalic acid of the formula

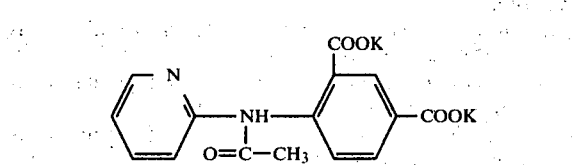

(b) A mixture consisting of 1 gm of the end product of step (a), 0.4 gm of potassium hydroxide, and 10 ml of water was refluxed for two hours, the resulting solution was evaporated, and the residue was triturated with ethanol/ether, whereby a crystalline product was obtained which was identified by NMR-spectrum analysis to be the compound of the formula

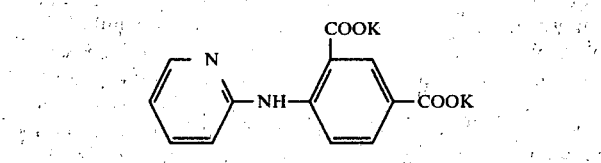

EXAMPLE 2

Disodium salt of 4-(2-pyridyl-amino)-isophthalic acid dihydrate by method B

A mixture consisting of 5.24 gm of 11H-11-oxo-pyrido[2,1-b]quinazoline-2-carboxylic acid and 20 ml of 1 N sodium hydroxide was heated for one hour on a water bath, whereby a clear yellow solution was obtained. The water was removed from the solution by azeotropic distillation with chloroform, and the crystalline residue was suspended in a little ether, suction-filtered off, and dried in vacuo at 60° C., yielding the compound of the formula

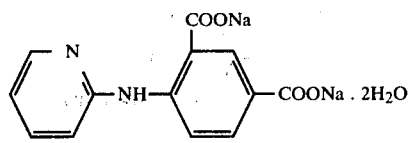

Elemental analysis: C₁₃H₈N₂O₄Na₂.2H₂O. Calc.: C—46.15%; H—3.55%; N—8.28%; H₂O—10.65%. Found: C—46.04%; H—3.34%; N—8.15%; H₂O—11.16%.

UV-spectrum:

| λ max | 288 nm | 328 nm |
|---|---|---|
| log ε | 4.18 | 4.30 |

EXAMPLE 3

Disodium salt of 2-(2-pyridyl-amino)-5-(1H-tetrazol-5-yl)-benzoic acid trihydrate by method B A mixture consisting of 8 gm of 11H-11- oxo-pyrido[2,1-b]-2-(1H-tetrazol-5-yl)-quinazoline and 60.6 ml of 1N sodium hydroxide was heated for two hours at 70° C. Thereafter, the water was distilled off, and the residual crystals were suspended in a little ether, suction-filtered off, and dried in vacuo at 60° C., yielding the compound of the formula

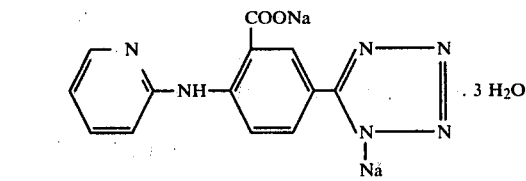

Elemental analysis: C₁₃H₈N₆O₂Na₂.3H₂O. Calc.: C—41.05%; H—3.68%; N—22.10%. Found: C—41.98%; H—3.54%; N—22.18%.

UV-spectrum:

| λmax | 290 nm | 317 nm |
|---|---|---|
| log ε | 4.24 | 4.27 |

Using procedures analogous to those described in Examples 1–3, the following additional compounds of the formula I and their sodium or disodium salts were prepared.

| Ex. No. | Nomenclature | Structural Formula | UV-Spectrum of Sodium Salt | |
|---|---|---|---|---|
| | | | λmax (nm) | log ε |
| 4 | 4-(2-pyridylamino)-isophthalic acid-1-monomethyl ester | | 288 326 | 4.18 4.40 |
| 5 | 4-(2-quinolinyl-amino)-isophthalic acid | | 292 355 | 4.32 4.34 |
| 6 | 6-(2-carboxy-4-methyl-phenyl-amino)-nicotinic acid | | 320 | 4.25 |
| 7 | 4-(2-pyridylamino)-isophthalic acid-1-mono-amide* | | 288 326 | 4.13 4.37 |
| 8 | 5-cyano-2-(2-pyridyl-amino)-benzoic acid | | 295 324 | 4.16 4.39 |
| 9 | 4-(2-pyridylamino)-isophthalic acid-1-monohydroxamic acid | | 292 324 | 4.20 4.26 |
| 10 | 2-(2-pyridylamino)-terephthalic acid | | 252 278 | 4.17 4.14 |
| 11 | 6-(2-carboxy-4-methoxyphenylamino)-nicotinic acid | | 310 | 4.21 |
| 12 | 6-(3-carboxy-2-naphthylamino)-nicotinic acid | | 275 326 | 4.32 4.32 |
| 13 | 4-(2-pyrimidyl-amino)-isophthalic acid | | 288 325 | 4.23 4.32 |
| 14 | 4-(5-amino-2-pyridylamino)-isophthalic acid | | 298 338 | 4.31 4.19 |
| 15 | 4-(5-acetamido-2-pyridylamino)-isophthalic acid | | 298 335 | 4.25 4.30 |

| Ex. No. | Nomenclature | Structural Formula | UV-Spectrum of Sodium Salt λmax (nm) | log ε |
|---|---|---|---|---|
| 16 | 4-(2-pyridylamino)-isophthalic acid-1-mono-N-(1H-tetrazol-5-yl)-carboxamide* | | 290 330 | 4.17 4.43 |
| 17 | N-butyrl-N-(2-pyridyl)-4-aminoisophthalic acid | | | |
| 18 | N-acetyl-N-(5-carboxy-2-pyridyl)-2-aminobenzoic acid | | | |
| 19 | N-acetyl-N-(5-carboxy-2-pyridyl) 2-aminobenzoic acid | | | |
| 20 | N-formyl-N-(2-pyridyl)-4-amino-isophthalic acid | | | |
| 21 | 6-(2-carboxyphenyl-amino)-nicotinic acid | | 325 | 4.30 |
| 22 | N-acetyl-N-(2-pyridyl)-4-amino-isophthalic acid | | 265 | 3.96 |

The UV-spectra were made with a Zeiss Spektralfotometer DMR 21. Accurately weighed 10–20 mgm samples of the compounds were dissolved in 0.01 N sodium hydroxide; in the case of those compounds marked with an asterisk (*), the compound was first dissolved in 10 ml of dimethylsulfoxide, and the resulting solution was diluted with 0.01 N sodium hydroxide. The long-wave absorption bands were chosen. The maximum absorption values, λ max (nm), together with the corresponding molar logarithmic extinction coefficients, log ε, are indicated.

The compounds of the present invention, that is, those embraced by formula I, their internal salts and their non-toxic, pharmacologically acceptable salts formed with basic substances, have useful properties. More particularly, they exhibit antiallergic activities in warm-blooded animals, such as rats and guinea pigs, and are therefore useful for prophylactic and therapeutic treatment of allergic conditions, such as asthma, hay fever, conjunctivitis, urticaria, eczema, atopic dermatitis and the like. In addition, they have muscle-relaxing (bronchodilator) and vasodilator properties.

The compounds of this invention are also useful as intermediates for the preparation of other drugs.

For pharmaceutical purposes the compounds of the present invention are administered to warm-blooded animals perorally, parenterally, topically, or by the respiration route as active ingredients in customary dosage unit compositions, that is, compositions in dosage unit form consisting essentially of an inert pharmaceutical carrier and an effective antiallergic amount of the active ingredient, such as tablets, coated pills, capsules, wafers, powders, solutions, suspensions, emulsions, syrups, creams, ointments, lotions, sprays and aerosols. The effective single dose or amount of the active ingredient in these compositions depends upon the indication, for example, the nature or severity of the allergic condition. In general, the single effective dose for administration by the respiratory route is about 2–40 mg; for parental administration it is about 0.2–8.0 mgm/kg; for oral administration it is about 0.6–16.0 mgm/kg; and for nasal or ocular administration it is about 2.5–75 mgm.

The following examples illustrate a few pharmaceutical compositions comprising a compound of the present invention as an active ingredient and represent the best modes contemplated of putting the invention into practical use. The parts are parts by weight unless otherwise specified.

EXAMPLE 23

Tablets

The tablet composition is compounded from the following ingredients:

| | |
|---|---|
| Disodium salt of 4-(2-pyridyl-amino)-isophthalic acid | 0.100 parts |
| Stearic acid | 0.010 parts |
| Dextrose | 1.890 parts |
| Total | 2.000 parts |

Preparation

The ingredients are intimately admixed with each other, and the mixture is granulated and compressed into 2 gm-tablets in conventional manner. Each tablet is an oral dosage unit composition containing 100 mgm of the active ingredient.

EXAMPLE 24

Ointment

The ointment is compounded from the following ingredients:
Disodium salt of 4-(2-pyridyl-amino)-isophthalic acid: 2.000 parts
Mixture of equal parts of cetyl alcohol and stearyl alcohol: 20.000 parts
White vaseline: 5.000 parts
Synthetic bergamot oil: 0.075 parts
Distilled water q.s. ad: 100.000 parts

Preparation

The ingredients are compounded in conventional manner into an ointment for topical application containing 2 gm of the active ingredient per 100 gm of ointment.

EXAMPLE 25

Inhalation aerosol

The aerosol composition is compounded from the following ingredients:
Dipotassium salt of 4-(2-pyridyl-amino)-isophthalic acid: 1.00 parts
Soybean lecithin: 0.20 parts
Propellant gas mixture (Frigen 11, 12 and 14) q.s.ad: 100.00 parts

Preparation

The ingredients are filled in conventional manner into pressurized aerosol cans equipped with a metering valve which discharges an amount of aerosol containing 5 mgm of the active ingredient with each actuation.

EXAMPLE 26

Hypodermic solution

The solution is compounded from the following ingredients:
Disodium salt of N-acetyl-N- (2-pyridyl)-4-amino-isophthalic acid: 10.0 parts
Sodium pyrosulfite: 1.0 parts
Disodium salt of EDTA: 0.5 parts
Sodium chloride: 8.5 parts
Double-distilled water q.s.ad: 1000.0 parts

Preparation

The active ingredient and the excipients are dissolved in a sufficient amount of double-distilled water, and the solution is diluted with additional double-distilled water to the desired concentration. The solution is then filtered until free from suspended particles, and the filtrate is filled into 1 cc-ampules under aseptic conditions, which are then sterilized and sealed. Each ampule contains 10 mgm of the active ingredient, and its contents are an injectable dosage unit composition.

For administration as an aerosol by the respiratory route, the active ingredients of the instant invention may also be filled in micronized form (particle size about 2–6 $\mu m$), optionally together with micronized inert carrier substances such as lactose, into hard gelatin capsules which are then inserted into conventional aerosol dispensing devices for powder inhalation. For instance, about 2 to 40 mgm of the active ingredient and 0 to 40 mgm of lactose are filled into each capsule.

Any one of the other compounds embraced by formula I, an internal salt thereof or a non-toxic, pharmacologically acceptable salt thereof may be substituted for the particular active ingredient in Examples 23 through 26. Likewise, the amount of active ingredient in these illustrative examples may be varied to achieve the dosage range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

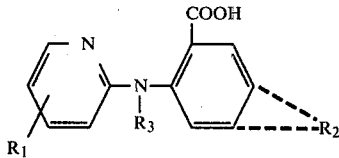

wherein
$R_1$ is (a) hydrogen, lower alkyl or lower alkoxy, or (b) —CO—$R_4$, tetrazol-5-yl or cyano in the 4- or 5-position;
$R_2$ is —CO—$R_4$, tetrazol-5-yl, cyano or, when $R_1$ has one of the meanings included in (b), also hydrogen, lower alkyl, lower alkoxy or a fused benzene ring;
$R_3$ is hydrogen or lower alkanoyl; and
$R_4$ is hydroxyl, amino, hydroxy-amino, tetrazol-5-yl-amino or lower alkoxy;
an internal salt thereof, or a non-toxic salt thereof formed with a basic substance.

2. The compound of claim 1, which is the disodium salt of 4-(2-pyridyl-amino)-isophthalic acid.

3. The compound of claim 1, which is the dipotassium salt of 4-(2-pyridyl-amino)-isophthalic acid.

4. The compound of claim 1 which is the disodium salt of 6-(2-carboxyphenylamino)-nicotinic acid.

5. An antiallergic pharmaceutical composition consisting essentially of an inert pharmaceutical carrier and an effective antiallergic amount of a compound of claim 1.

6. The method of preventing or relieving allergic reaction in a warm-blooded animal in need thereof, which comprises perorally, parenterally, topically or by the respiratory route administering to said animal an effective antiallergic amount of a compound of claim 1.

* * * * *